US012329498B2

(12) United States Patent
Huber

(10) Patent No.: US 12,329,498 B2
(45) Date of Patent: Jun. 17, 2025

(54) INFRARED VISUALIZATION OF CARDIAC AND PULMONARY ACTIVITY

(71) Applicant: JuvaTech, LLC, Toledo, OH (US)

(72) Inventor: Robert Huber, Toledo, OH (US)

(73) Assignee: JuvaTech, LLC, Toledo, OH (US)

( * ) Notice: Subject to any disclaimer, the term of this patent is extended or adjusted under 35 U.S.C. 154(b) by 540 days.

(21) Appl. No.: 17/602,498

(22) PCT Filed: Apr. 9, 2020

(86) PCT No.: PCT/US2020/027389
§ 371 (c)(1),
(2) Date: Oct. 8, 2021

(87) PCT Pub. No.: WO2020/210435
PCT Pub. Date: Oct. 15, 2020

(65) Prior Publication Data
US 2022/0211279 A1    Jul. 7, 2022

Related U.S. Application Data

(60) Provisional application No. 62/831,937, filed on Apr. 10, 2019.

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02416* (2013.01); *A61B 5/0816* (2013.01);
(Continued)

(58) Field of Classification Search
CPC . A61B 5/0205; A61B 5/02416; A61B 5/0816; A61B 5/4848; A61B 5/4884;
(Continued)

(56) References Cited

U.S. PATENT DOCUMENTS

| 2004/0187169 A1 | 9/2004 | Paternostro |
| 2006/0247862 A1 | 11/2006 | Arini et al. |

(Continued)

FOREIGN PATENT DOCUMENTS

| EP | 3339856 A1 | 6/2018 |
| GB | 2541280 A | 2/2017 |

(Continued)

OTHER PUBLICATIONS

Guo, S. Y. et al. "Semiautomatic and rapid quantification of heartbeat parameters in *Drosophila* using optical coherence tomography imaging." Journal of Biomedical Optics. 18(2), 026004 (2013). (Year: 2013).*

(Continued)

*Primary Examiner* — John R Wallace
(74) *Attorney, Agent, or Firm* — MacMillan, Sobanski & Todd, LLC

(57) ABSTRACT

Methods of analyzing cardiac and/or pulmonary activity of an animal involving the use of video under infrared illumination, and systems for monitoring cardiac and/or pulmonary activity of an animal, are described.

19 Claims, 11 Drawing Sheets
(6 of 11 Drawing Sheet(s) Filed in Color)

(51) Int. Cl.
   *A61B 5/024* (2006.01)
   *A61B 5/08* (2006.01)
(52) U.S. Cl.
   CPC .......... *A61B 5/4848* (2013.01); *A61B 5/4884* (2013.01); *A61B 5/7203* (2013.01); *A61B 2503/40* (2013.01)
(58) Field of Classification Search
   CPC .............. A61B 5/7203; A61B 2503/40; A61B 5/02433; A61B 5/1128; A61B 5/113; A61B 5/0077; A61B 5/08
   See application file for complete search history.

(56) References Cited

U.S. PATENT DOCUMENTS

| | | | |
|---|---|---|---|
| 2014/0272764 A1* | 9/2014 | Miller | A61B 1/051 433/29 |
| 2017/0310901 A1 | 10/2017 | Sheikh et al. | |
| 2018/0078195 A1 | 3/2018 | Sutaria et al. | |
| 2018/0322941 A1 | 11/2018 | Krishnan et al. | |

FOREIGN PATENT DOCUMENTS

| | | |
|---|---|---|
| KR | 20140082756 A | 7/2014 |
| WO | 2010144494 A2 | 12/2010 |

OTHER PUBLICATIONS

Lee, Chia-Yen et al. "Automated Drosophila Heartbeat Counting Based on Image Segmentation Technique on Optical Coherence Tomography." Scientific reports 9.1 (2019): 5550-5557. (2019). (Year: 2019).*

Monck, Hauke. "A new method to characterize function of the Drosophila heart by means of optical flow." Journal of Experimental Biology (2017) 220, 4644-4653. (2017). (Year: 2017).*

G. Paternostro et al., "Age-associated cardiac dysfunction in *Drosophila melanogaster*." Circ. Res. 88(10), 1053-1058 (2001). (Year: 2001).*

Wasserthal, L. T., "*Drosophila* flies combine periodic heartbeat reversal with a circulation in the anterior body mediated by a newly discovered anterior pair of ostial valves and venous channels." The Journal of Experiemental Biology. 210, 3707-3719 (2007). (Year : 2007).*

Fang Zhao, Meng Li, Yi Qian, and Joe Z Tsien, "Remote measurements of heart and respiration rates for telemedicine." PloS one, vol. 8, No. 10, pp. e71384. (2013). (Year: 2013).*

Aumann, Silke. "Optical Coherence Tomography (OCT): Principle and Technical Realization." Springer eBooks. Springer Nature (2019), 59-85. (Year: 2019).*

Israelsen, Niels M et al. "Real-Time High-Resolution Mid-Infrared Optical Coherence Tomography." Light, science & applications 8.1 (2019), 1-13. (Year: 2019).*

Reinhardt, "Development of a System to Measure Cardiac Function in the *Drosophila melanogaster* Animal Model", New Jersey Institute of Technology; Publication [online]; Spring 2006 [retrieved Jun. 12, 2020]. Retrieved from the Internet; <URL; https://digitalcommons.njit.edu/cgi/viewcontent.cgi?article=1433&context=theses>; pp. 1-100.

Arlotto et al., "An Ultrasonic Contactless Sensor for Breathing Monitoring", Sensors, 2014, vol. 14, pp. 15371-15386.

Turin et al., "Electron spin changes during general anesthesia in *Drosophila*", PNAS, Published [online] Aug. 11, 2014, [retrieved Jun. 12, 2020], Retrieved from Internet: <URL:https://www.pnas.org/content/pnas/111/34/E3524.full.pdf>; pp. ES524-ES533.

Burke, "Layered Reward Signalling Through Octopamine and Dopamine in *Drosophila*: A Dissertation", University of Massachusetts Medical School; Publication [online] May 10, 2013, [retrieved Jun. 12, 2020]. Retrieved from Internet: <URL:https://escholarship.umassmed.edu/cfi/viewcontent.cgi?article=1659&context=gsbs_diss>; pp. 1-100.

Ocorr et al., "Methods to assess *Drosophila* heart development, function and aging", National Institute of Health Public Access; Publication [online] Jun. 15, 2014 [Retrieved Jun. 11, 2020]. Retrieved from the Internet: <URL:https:www.hcbi.nlm.nih.gov/pmc/articles/PMC4058868/>; pp. 1-21.

Murphy et al., "Simultaneous measurement of sleep and feeding in individual *Drosophila*", HHS Public Access; Publication [online] Oct. 12, 2017; Retrieved from the Internet: <URL:https:www.https://www.ncbi.nlm.nih.gov/pmc/articles/PMC5812262/>; pp. 1-25.

Pautsina et al., "Noninvasive crayfish cardiac activity monitoring system", Limnology and Oceanography: Methods, 2014, vol. 12, pp. 670-679.

International Search Report and Written Opinion, Application No. PCT/US2020/27389, dated Jul. 22, 2020.

* cited by examiner

INFRARED VISUALIZATION OF CARDIAC AND PULMONARY ACTIVITY

RELATED APPLICATIONS

This is the national phase entry of international application PCT/US20/027389, filed under the authority of the Patent Cooperation Treaty on Apr. 9, 2020, published; which claims priority to U.S. Provisional Application No. 62/831,937, filed under 35 U.S.C. § 111(b) on Apr. 10, 2019. The entire disclosure of each of the aforementioned applications is incorporated herein by reference for all purposes.

STATEMENT REGARDING FEDERALLY SPONSORED RESEARCH

This invention was made with no government support. The government has no rights in this invention.

BACKGROUND

The *Drosophila* cardiac system is a useful model for examining a wide range of issues concerning the functioning of the human heart. The fly model has become a highly productive experimental framework for identifying the mechanisms underlying congenital heart diseases, cardiac myopathies, and the underlying genetic and physiological determinants of heart function. Important among these are age-related changes reflected in a wide range of physiological metrics. Opioid overdose causes death with the depression of breathing and heartbeat. The fly heart offers a suitable model to explore the physiological mechanisms in drug related death and offers a viable screen to identify and test promising therapeutic interventions.

Existing methods for the analysis of cardiac and pulmonary function in adult flies include optical, electrophysiological, and mechanical approaches to measure changes in cardiac tissue and tracheal properties. However, current methods are highly invasive and require dissection of the animal with in vivo recordings made from semi-intact preparation. Thus, there is a need in the art for new and improved methods for analyzing cardiac and pulmonary function in flies and other animals.

SUMMARY

Provided is a method for analyzing cardiac and/or pulmonary activity of an animal, the method comprising obtaining video of an anatomical region of an animal under infrared illumination to produce a stream of images; and identifying a recurrent pattern in the stream of images of the anatomical region, wherein the recurrent pattern corresponds to a heartbeat and/or breathing of the animal. In certain embodiments, the animal is a fly, and the anatomical region is a neck region of the fly. In certain embodiments, the animal is free of any external sensors or markers. In certain embodiments, the animal is immobilized.

In certain embodiments, the animal is a fruit fly. In certain embodiments, the animal is a human, a mouse, a fish, or an earthworm.

In certain embodiments, the recurrent pattern has a frequency of <1 Hz and corresponds to breathing of the animal. In particular embodiments, the recurrent pattern has a frequency of about 0.1 Hz.

In certain embodiments, the recurrent pattern has a frequency of 1-6 Hz and corresponds to the heartbeat of the animal. In particular embodiments, the recurrent pattern has a frequency of about 1.5 Hz.

In certain embodiments, the video is obtained at a frame rate of at least about 40 frames per second. In certain embodiments, the video is obtained at a frame rate of about 60 frames per second. In certain embodiments, the video is obtained with a video camera that produces uncompressed images.

In certain embodiments, the stream of images is assembled into an array of individual pixel vectors. In particular embodiments, the individual pixel vectors are filtered to enhance a signal-to-noise ratio and produce filtered images. In particular embodiments, the filter comprises a low-pass (<1 Hz) or a band-pass (1-6 Hz) filter to reduce variability in each pixel record outside the range for heartbeat or breathing. In particular embodiments, the recurrent patterns are identified in the filtered images.

In certain embodiments, the rhythmic patterns for breathing are identified in the frequency band below 1 Hz. In certain embodiments, the rhythmic patterns for heartbeat are identified in the frequency band of 1-6 Hz.

In certain embodiments, the strength of the recurring pattern(s) is identified with a fourier transform. In certain embodiments, rhythmic patterns in <1 Hz or 1-6 Hz range are identified.

In certain embodiments, the infrared illumination is provided by one or more near-IR LEDs. In certain embodiments, the infrared illumination is provided by an LED having a wavelength of about 850 nm, about 940 nm, or about 1050 nm.

In certain embodiments, the method further comprises graphing sums of unfiltered and filtered pixel values for the anatomical region over time.

In certain embodiments, nothing is physically attached to the animal to analyze the cardiac activity or pulmonary activity of the animal.

Further provided is a method of testing a pharmaceutical compound on an animal, the method comprising administering a pharmaceutical compound to an animal; observing the animal with video under infrared illumination to produce a stream of images; and identifying a recurrent pattern in the stream of images, wherein the recurrent pattern corresponds to a heartbeat or breathing of the animal, to determine an effect of the pharmaceutical compound on the animal. In certain embodiments, an anatomical region other than a heart region of the animal is observed. In certain embodiments, the animal is a fly and a neck region of the fly is observed. In certain embodiments, the animal is observed without any markers or sensors attached to the animal. In certain embodiments, the animal is immobilized. In certain embodiments, the animal is a fruit fly. In certain embodiments, the animal is a human, a mouse, a fish, or an earthworm. In certain embodiments, the video is obtained at a frame rate of at least about 40 frames per second. In certain embodiments, the video is obtained at a frame rate of about 60 frames per second.

Further provided is a method of evaluating a stimulus on an animal, the method comprising observing an animal with video under infrared illumination to produce a stream of images; applying a stimulus to the animal while observing the animal with video; and identifying a recurrent pattern in the stream of images, wherein the recurrent pattern corresponds to a heartbeat or breathing activity of the animal, to determine an effect of the stimulus on the heartbeat or breathing of the animal. In certain embodiments, the stimulus comprises exposure to light, heat, cold, an odor, physical touching, or a sound. In certain embodiments, the stimulus provides a stressful condition with administration of electric shock, social interactions with other individuals, or unsuited environmental conditions. In certain embodiments, an anatomical region other than a heart region of the animal is observed. In certain embodiments, the animal is a fly and a neck region of the fly is observed. In certain embodiments, the animal is observed without any markers or sensors attached to the animal. In certain embodiments, the animal is immobilized.

Further provided is a system for monitoring cardiac activity of an animal, the system comprising an enclosure, a light source configured to illuminate the enclosure with infrared or near-infrared light; a video camera adapted to obtain video of an animal housed within the enclosure; and a computing system communicatively coupled to the video camera, wherein the computing system is capable of identifying a recurrent pattern in the video obtained by the video camera that corresponds to a heartbeat or breathing of the animal. In certain embodiments, the system is free of any sensors or markers configured to be attached to the animal. In certain embodiments, the system further comprises an interface board configured to translate pixels received from the video camera into data stored in a memory.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows an image of the fly with the neck region marked. FIG. 2B shows a detail view of the neck region. FIG. 2C shows a detail view of the neck region with activity in the cardiac activity band of 1-6 Hz indicated by darker colors. FIG. 2D shows a detail view of the neck region with activity in the pulmonary activity band of <1 Hz indicated by darker colors.

FIG. 3A shows an unfiltered trace. Slow baseline drifts and high frequency noise arise from a combination of imaging chip noise, changes in lighting intensity, and physical vibrations. FIG. 3B shows the cardiac-filtered trace. FIG. 3C shows the pulmonary-filtered trace.

FIG. 4A shows the unfiltered fourier spectrum. FIG. 4B shows the cardiac-filtered fourier spectrum, which reveals a recurring pattern around 1.7 Hz, indicative of the heartbeat. FIG. 4C shows the pulmonary-filtered fourier spectrum, which reveals a recurring pattern around 0.1 Hz, indicative of the animal's breathing.

DETAILED DESCRIPTION

Figure 1:
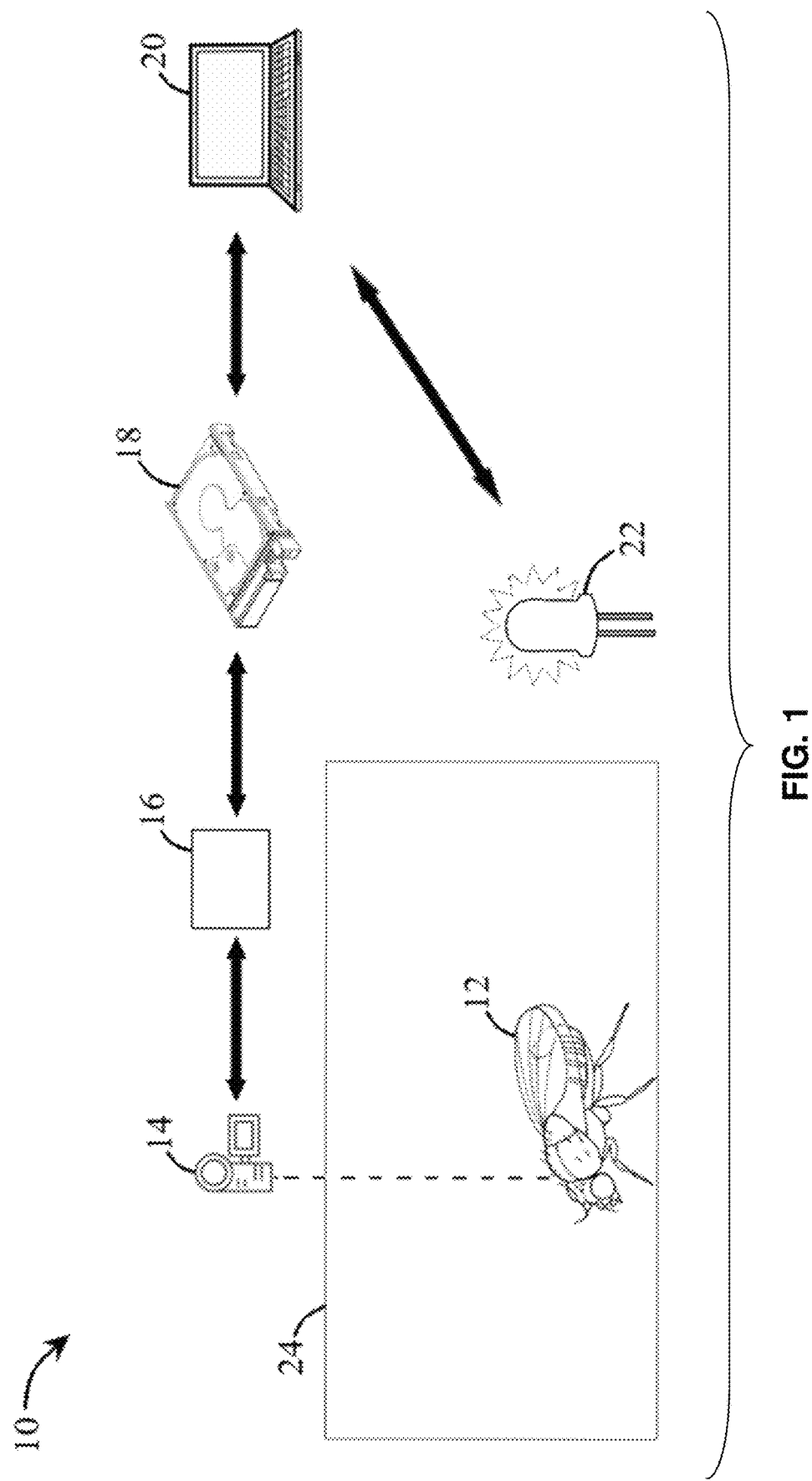
FIG. 1: Illustration of a non-limiting example system for monitoring cardiac and breathing activity of an animal.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

In accordance with the present disclosure, cardiac and/or pulmonary activity of an animal may be monitored by monitoring changes in infrared (IR) reflectance using an IR-sensitive camera system. The present disclosure allows for the monitoring of cardiac and pulmonary activity in intact, freely-behaving animals. Changes in IR reflectance may be measured from image streams of specific anatomical regions of the animal. The anatomical regions may be regions other than the heart region of the animal. For example, the anatomical region may be a neck region of the animal. Changes in heartbeat or breathing can be processed using an optical signal. No external sensors or markers need to be placed on the animal to do this; nothing needs to be physically attached to the animal. The ability to non-invasively monitor cardiac and pulmonary function in intact individuals allows for performing longitudinal studies that are important for exploring phenomena such as, but not limited to, the effects of life events such as stressors, the emergence of myopathic traits in development, heart failure from pharmacological insults such as opioid drugs, age-related changes in cardiac function, and the effectiveness of drug therapies in countering these effects.

In some embodiments, a method herein involves obtaining video of an anatomical region of an animal under infrared illumination to produce a stream of images, and identifying a recurrent pattern in the stream of images of the anatomical region, where the recurrent pattern reflects the heartbeat or breathing of the animal. The method may be utilized to monitor only the heartbeat, to monitor only breathing, or to monitor both the heartbeat and breathing. Using a video camera under IR illumination, repeating cycles of contractions/expansions of the blood vessels and tracheae supplying the head of the animal can be observed. Without wishing to be bound by theory, it is believed that this is possible because blood has proteins with metals in them, and so there is a stronger reflection of light wherever blood is. As the heart expands, a larger area reflects back IR light, and as the heart or blood vessel contracts, the signal is diminished. Heartbeat and breathing both produce recurrent patterns that can be identified in a stream of images obtained under IR illumination, and are represented in different frequency bands which can be sorted out through filtering.

The ability to monitor cardiac and pulmonary activity in animals is of interest for many reasons, including pharmaceutical compound testing. The methods described herein are advantageous compared to known methods of monitoring cardiac or pulmonary activity of animals. The present disclosure provides the ability to monitor cardiac and pulmonary function in intact animals such as fruit flies using video imaging, without the need to physically touch the animal or attach anything to the animal. In contrast, known methods may involve physically attaching a sensor which combines an IR transmitter and a transceiver for the reflected signal to the animal being monitored. However, as described herein, it is not necessary to physically attach anything to the animal in order to monitor its heart rate or breathing. Rather, the heart rate or breathing of an animal can be monitored with a video camera under IR illumination.

Referring now to FIG. 1, depicted is a non-limiting example system 10 for analyzing cardiac activity or pulmonary activity of an animal 12. The system 10 may include a video camera 14, an interface board 16, a memory 18, a computing device 20, a light source 22, and an environment 24 where an animal 12 is located, such as an enclosure housing the animal 12. The double-sided arrows in FIG. 1 illustrate that any of the functional components of the system 10 may be communicatively coupled. Advantageously, there is no need for any physical attachments (such as markers or sensors) to the animal 12 to monitor the cardiac activity or pulmonary activity as described herein.

Capturing uncompressed, grayscale, 8-bit images to a memory 18 such as a hard disk at high frame rates is a challenging task. A very small signal may be extracted from a noisy system. This may involve the complex processing of a large body of frame data. Suitable video hardware for doing this may include a specially designed video camera 14 and interface board 16.

The video camera 14 should be capable of producing uncompressed images and have a frame rate of at least about 40 fps. The video camera 14 should produce uncompressed images, at least 8-bit, and save them to memory 18 with a frame rate of at least about 40 fps. A frame rate of at least about 40 fps is important because a heartbeat has a frequency of about 1.7 Hz, and breathing has a frequency of about 0.1 Hz, and the frame rate should be significantly above the frequency of the heartbeat and breathing. There is no maximum to the possible frame rate. In some embodiments, the frame rate is 60 fps, which has been found to provide suitable results capable of filtering. Suitable video cameras 14 include some commercially available USB 3.0 cameras. One non-limiting example of a suitable video camera 14 that is commercially available is the ThorLabs DCC3240M—High-Sensitivity USB 3.0 CMOS Camera, 1280×1024, Global Shutter, Monochrome Sensor.

The video camera 14 does not need RGB. Changes in IR reflectance of specific anatomical regions of the animal 12 may be obtained from monochrome images recorded at a frame rate of at least about 40 fps, though a higher frame rate of 60+ fps may provide better results. Typical video cameras having high frame rates compress images in a way that changes the gray scale pixel values. However, the video camera 14 should provide uncompressed images. There is a tradeoff between lower compression, higher image resolution and higher frame rate. In one non-limiting example, a 640×480 pixel system is used. The higher the resolution, the fewer the frames.

The interface board 16 translates pixels received from the video camera 14 into data and sends the data to the memory 18 for storage. In some embodiments, the interface board 16 translates the incoming stream of pixels into something that can be transferred over USB to the memory 18. The interface board 16 groups the bit-information representing pixel grayscales into values. Suitable interface boards 16 may be purchased commercially. In some embodiments, the interface board 16 is built-in to the video camera 14 and is not a separate piece of hardware. The memory 18 may be RAM, ROM, a flash memory, a hard drive, or any means of storing machine readable instructions received from the video camera 14 via the interface board 16. The memory 18 may optionally be within the computing system 20, though need not be.

The interface board 16 and the memory 18 may be communicatively coupled to a computing system 20, which may be a computer or smart device such as a tablet. The computing system 20 may take the form of any device or devices capable of processing and filtering the stream of images to identify a recurrent pattern in the stream of images. When performed in real time, the processing of a massive number of pixel data, and the band-pass filtering of the signal, places significant demands on computing hardware. As a non-limiting example, a networked cluster of Linux CPUs may be utilized for this task. Signal extraction may be performed with a combination of custom Linux-based software developed for this purpose and open source frameworks such as R (R Core Team, R Foundation for Statistical Computing, Vienna, Austria). However, other methods are possible.

The stream of images from the video camera 14 may be assembled into an array of individual pixel vectors, which may be filtered to enhance the signal-to-noise ratio and produce filtered images. The filters may include a band pass filter, or a high-pass filter followed by a rolling average filter to reduce high-frequency noise in each pixel record. The strength of the recurring pattern, which corresponds to the heartbeat or breathing of the animal, can be identified in the filtered images, for example with a fourier transform. In some embodiments, rhythmic patterns in different frequency bands contain cardiac activity, in a 1-6 Hz range, and breathing, in a <1 Hz range.

Referring still to FIG. 1, the animal 12 may be observed in an environment 24 illuminated with IR or near-IR lighting from a light source 22. While the number and distribution of light sources 22 is not particularly limited, infrared illumination should be of sufficient intensity to penetrate through the carapace of the fly (or skin or whatever animal is being monitored) and reflect back to the video camera, but not so intense so as to overly heat or otherwise harm the animal. The light source 22 may be one or more near-IR LEDs. In some embodiments, the lighting has a wavelength of about 850 nm, about 940 nm, or about 1050 nm. The shorter the wavelength of the light, the less the light will penetrate the carapace or skin of the animal 12. The longer the wavelength of the light, the more energy will pass through the carapace or skin of the animal 12. The angle of the lighting may optimize the results, but is not critical in being able to observe the heartbeat or breathing.

The animal 12 may be housed in a controlled environment 24, such as an enclosed chamber, while being observed with video. The lighting from the light source 22 may be provided from either inside or outside of the controlled environment 24. The animal 12 may be housed in a chamber which allows full visibility of the animal 12 by the video camera 14. Multiple animals 12 may be included in environment 24 and tracked in separate areas or tracked individually in a common space. When monitoring flies, individual fly chambers may be vertically or horizontally arranged to allow visual access to multiple flies from a single video camera 14. Plexiglass is sufficiently strong and transparent for infrared light to allow for visual observation, but other materials may be used to form the environment 24 housing the animal 12. In some embodiments, the video camera 14 may be positioned about 1-2 inches from the animal 12. However, the distance between the animal 12 and the video camera 14 may vary depending on the focal length of the lens in the video camera 14. Longer focal lengths allow for greater distance between fly and camera, but result in a shorter depth of field and reduce the amount of light coming in.

Heartbeat and breathing may provide a general indication of metabolic status, and may signal the impact of external stressors. *Drosophila* is commonly used for the dissection of genetic and neuronal mechanisms of behavior. Flies are a model for investigating numerous phenomena. In particular, fly hearts provide a close experimental model of human hearts. Flies are suitable for high throughput studies, require little space, are low-cost, avoid some ethics concerns of research using mammals, and offer attractive life history traits. Also, a life span of about 60 days provides a useful system for the study of aging. However, the animal 12 does not need to be a fly. The animal 12 can be a fruit fly, a human, a mouse, a fish, or an earthworm, as some non-limiting examples. Many other animals 12 are possible. When monitoring flies, it is helpful, though not critical, to obtain a view of the back of the neck of the adult fly. This will produce less noise than observing other areas of the fly. Advantageously, flies do not have a lot of pigmentation in the area of interest. It is, however, nonetheless possible to observe other areas of the fly, such as the abdomen, and still obtain the heartbeat and breathing activity. When utilizing animals 12 such as rats, it may be advantageous to shave the anatomical region being observed to allow for better IR penetration. However, this is not strictly necessary.

Female flies are generally twice the size of male flies, and so may be easier to analyze. Also, when monitoring the cardiac activity of flies, the flies may be placed on fly paper to reduce movement (i.e., to immobilize the flies). Alternatively or in addition, tracking software may be utilized. Freely moving animals may be tracked using standard image analysis techniques. Suitable tracking software may include commercially available or open source software such as JavaGrinders, which is an open-source, Java-based framework. In another non-limiting example, the open source imaging library OpenCV is used to track animals. The same anatomical region on the fly can be found from frame to frame with tracking software, even if the fly moves around the area.

The method also provides the ability to monitor cardiac and/or pulmonary activity in multiple animals at once. As will be appreciated by those of skill in the art, the number of animals capable of being monitored at once depends on various factors such as the size of the animal.

The method described herein is especially useful for pharmaceutical testing using animals such as fruit flies as a model system. The method can be employed to see how the heart or pulmonary system physiologically changes with exposure to a test compound, or from aging or other factors. For example, compounds may be tested on the flies while monitoring their cardiac and pulmonary function to evaluate the effects of the compounds, thus allowing for inexpensive and useful pharmaceutical compound testing. In one non-limiting example experiment, the heartbeat and breathing of a fly can be observed after administering a drug to the fly. In other examples, multiple strains of flies may be observed simultaneously to determine differences in the effects on heartbeat between genetically different strains. In other examples, specific genetic mutants of flies may be observed to determine differences in the effects on heartbeat and breathing as a result of genetic modifications.

The system and method described herein are by no means limited to pharmaceutical testing. Rather, the present disclosure can be used to evaluate the effect of any stimulus on the heartbeat or breathing of an animal. In general, an animal can be observed with video under infrared illumination to produce a stream of images, a stimulus may be applied to the animal while observing the animal with video, and then a recurrent pattern in the stream of images may be identified, where the recurrent pattern corresponds to the heartbeat or breathing of the animal, in order to determine the effect of the stimulus on the heartbeat or breathing of the animal Non-limiting examples of stimuli include exposure to light, heat, cold, an odor, physical touching, or a sound. Non-limiting examples of stimuli also include stressors such as electric shocks, food or water deprivation, social stress, or environmental conditions outside the normal range.

The present disclosure permits long-term, continuous monitoring of cardiac and breathing activity, and may be utilized on animals which enable high-throughput and low-cost analysis. Unlike the known method which combines an IR transmitter and a transceiver, it is not necessary that anything be attached to the animal being observed. This is highly advantageous, for instance because an IR transmitter and transceiver cannot easily be attached to certain animals such as flies whose cardiac and pulmonary systems serve as model systems for humans.

Examples

Materials and Methods

Fly Handling

Berlin K (BK) wild type male and female flies were used in these examples. All flies were raised on a cornmeal-sucrose-agar food in a 25° C. incubator with a 12-hr Light/Dark cycle and were 3-5 days old at the start of each experiment. Flies were selected under $CO_2$ or cold anesthesia and placed into a circular, shallow bowl-shaped recording arena (10 mm diameter, 2 mm) covered with a glass cover slip. In several experiments the fly was fixed in place with a strip of fly paper at the bottom of the arena. The arena was positioned inside of an environmental chamber under a USB video camera.

Video Hardware

The fly was recorded under a USB video camera (Arducam CMOS MT9V022 ⅓-inch 0.36 MP monochrome with ArduCAM USB3 camera shield and custom MIPI adapter board). Lighting was provided by near-infrared LEDs (940 nm Infrared Emitter, 1.65 V, 100 mA, Vishay Semiconductor Opto Division) soldered onto custom PCB lighting boards designed in-house and manufactured at WellPCB PTY Ltd (Shijazhuang, China), placed at 45 degrees from above.

Data Capture

Image capture was provided with a custom C++ application that acquired a series of raw pixel images at a stream rate of 60 frames per second and logged them as individual files to a hard disk for subsequent analysis. The primary recording hardware used for this task were a MintBox Mini 2 Pro (Quad-core Celeron J3455, 8 GB RAM, 120 GB SSD; Compulab, Yokneam, Israel) and a Lattepanda Alpha 864 (DFRobot, Pudong, Shanghai, China).

Data Analysis

Figure 2A:
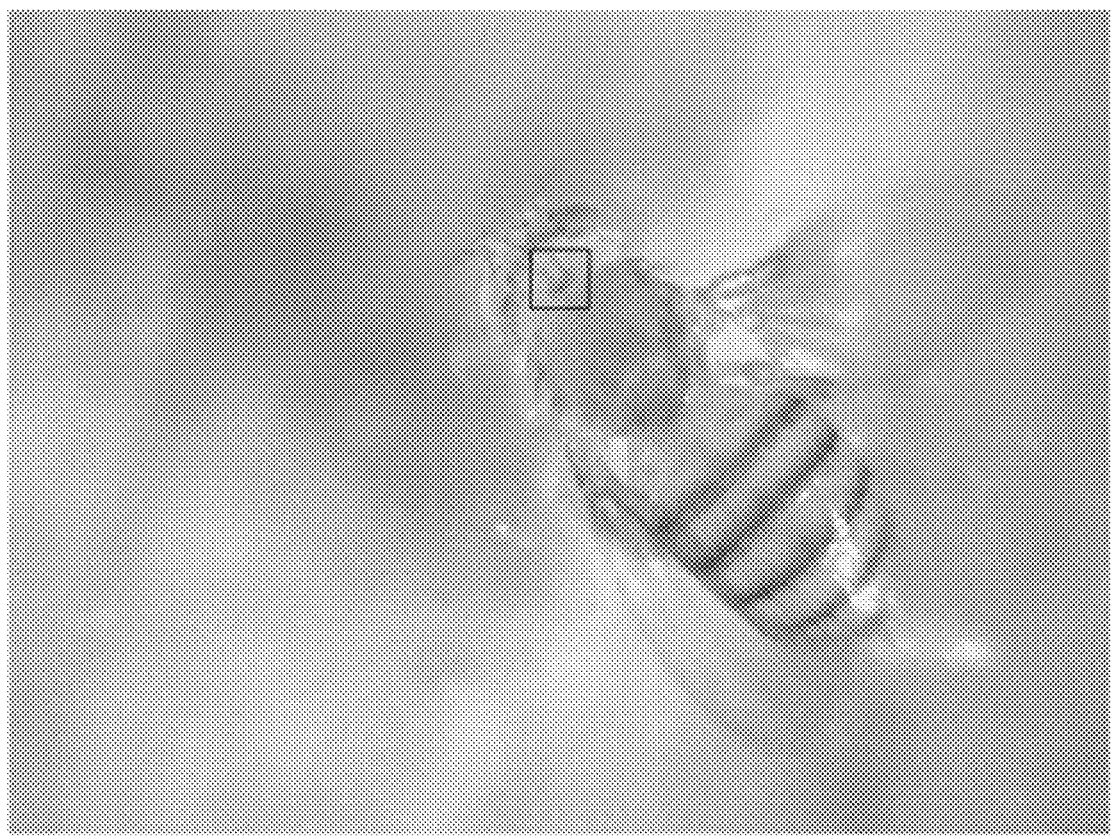
FIGS. 2A-2D: Images of a fly being monitored for cardiac and pulmonary activity. Regions around the wing and abdomen exhibit a lot of movement artifacts, while the neck region includes an area in which the heartbeat and breathing are reliably observed.
Figure 2B:
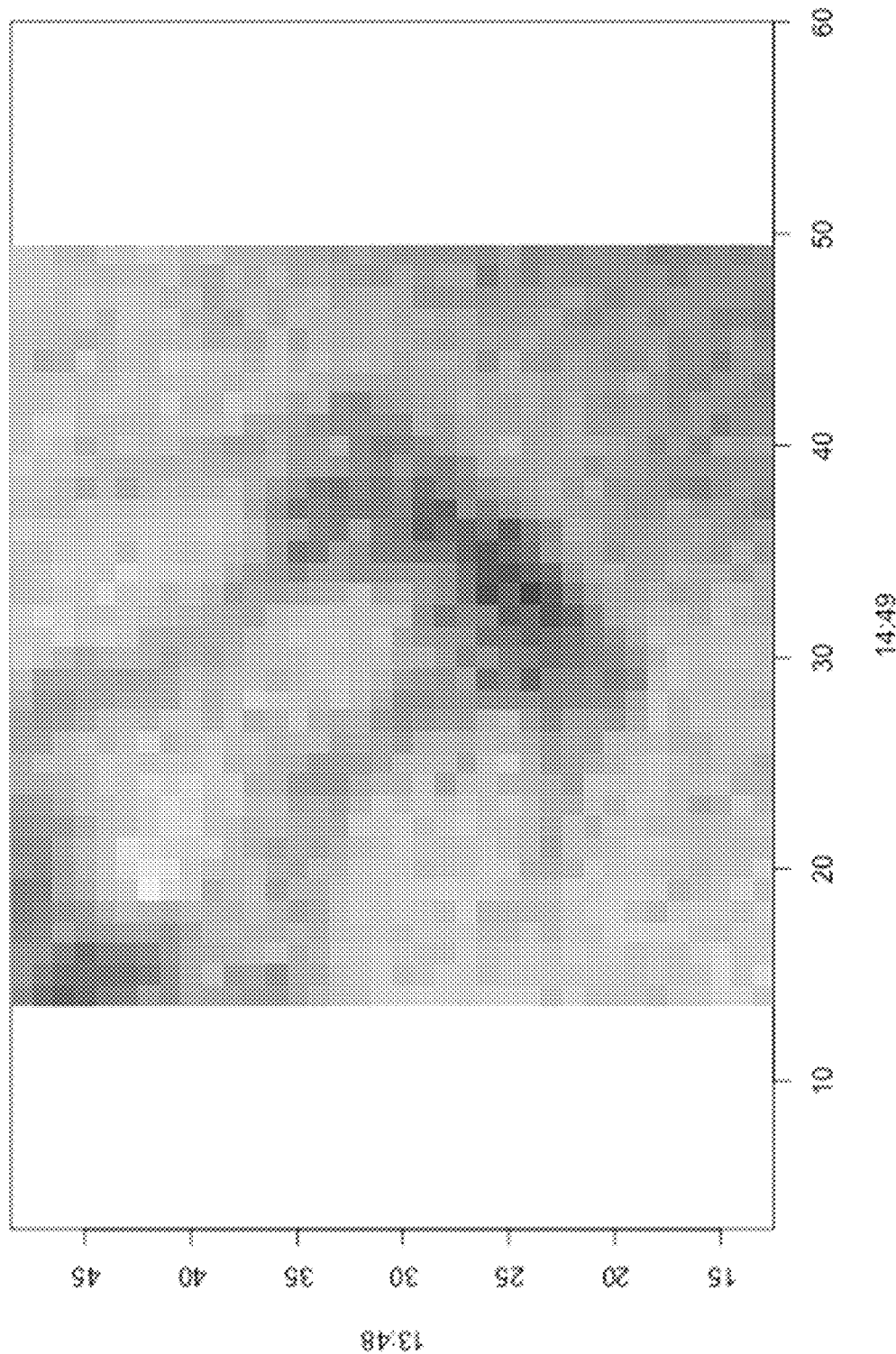
Figure 2C:
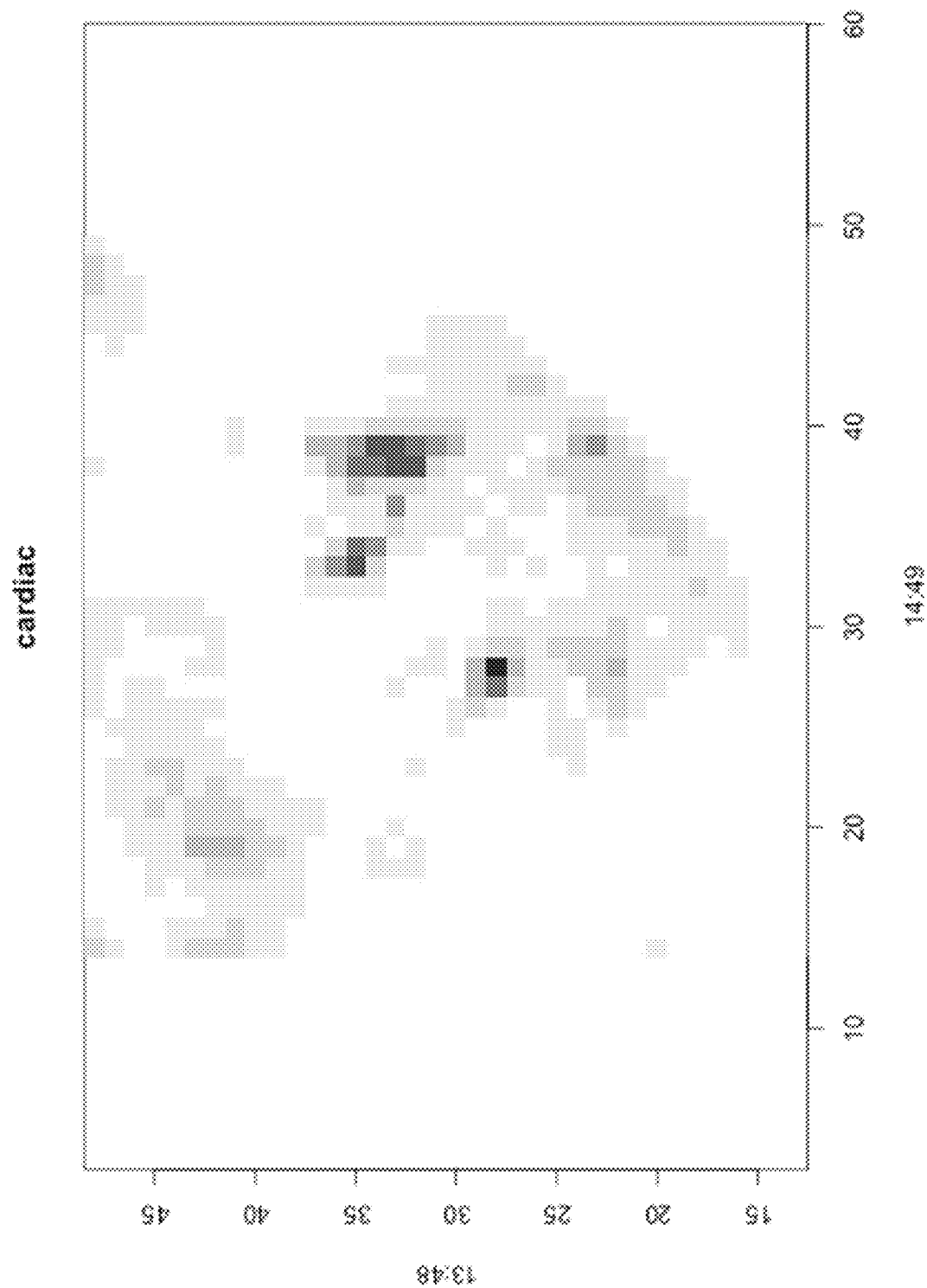
Figure 2D:
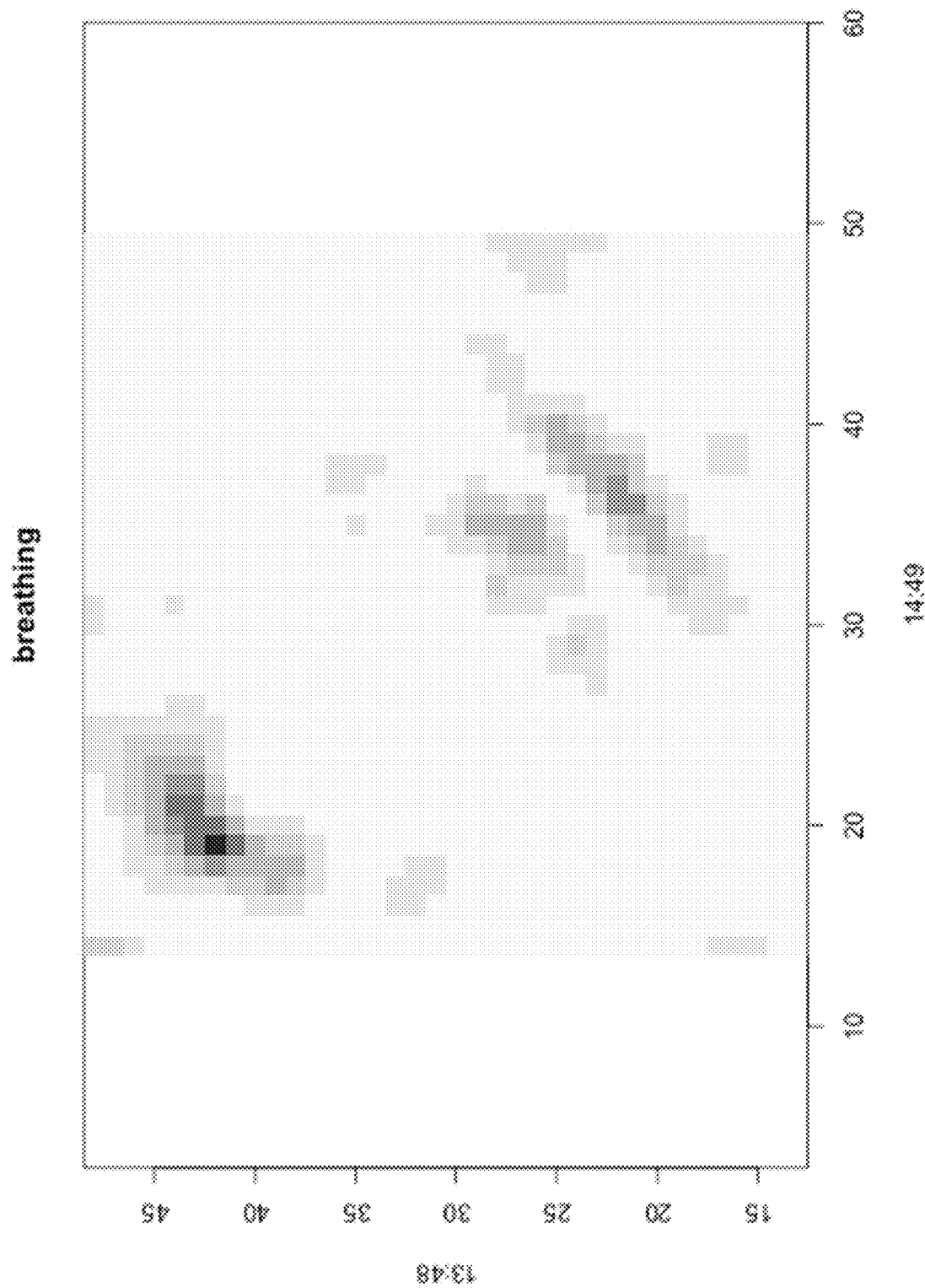
Figure 3A:
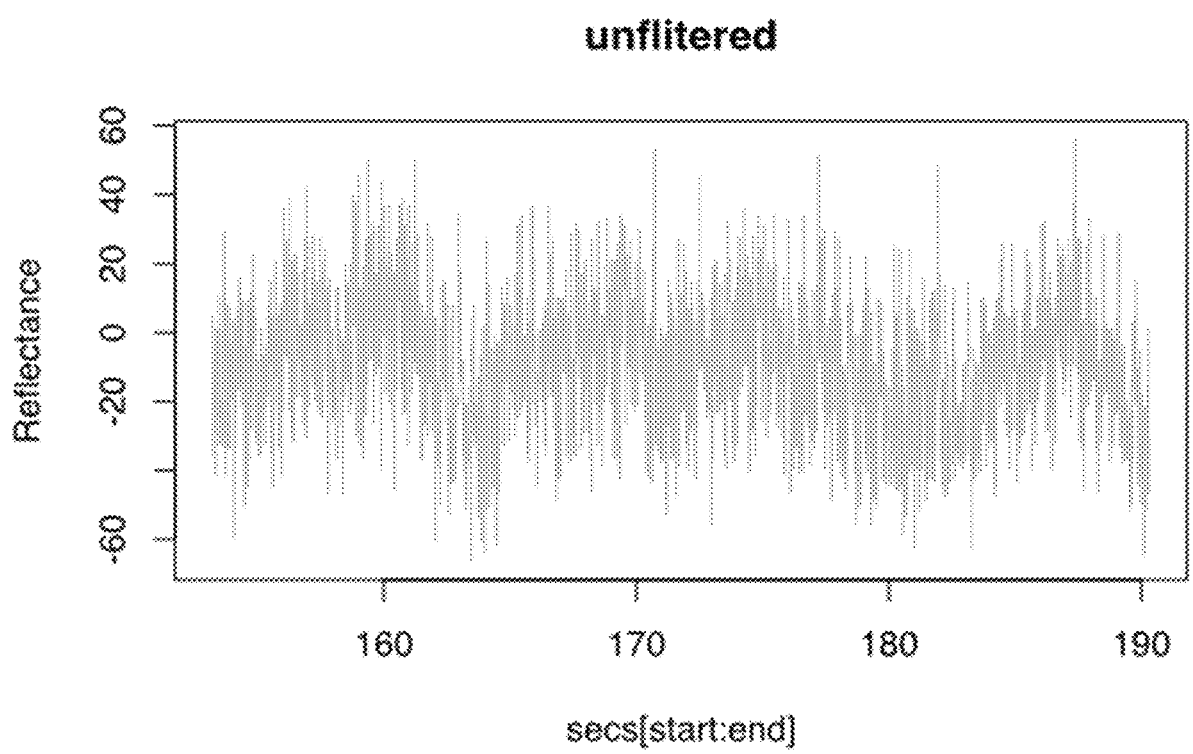
FIGS. 3A-3C: Traces obtained from the fly neck region, immediately proximal to the head-thorax attachment, with a 40-second representation of the signal before and after filtering.
Figure 3B:
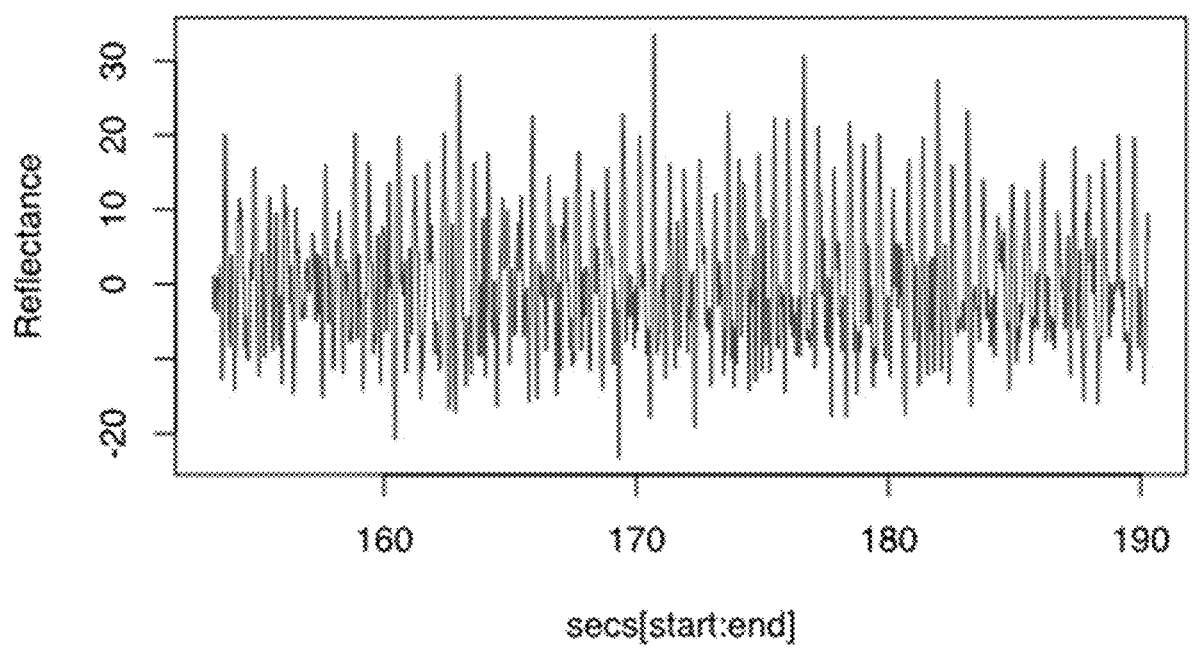
Figure 3C:
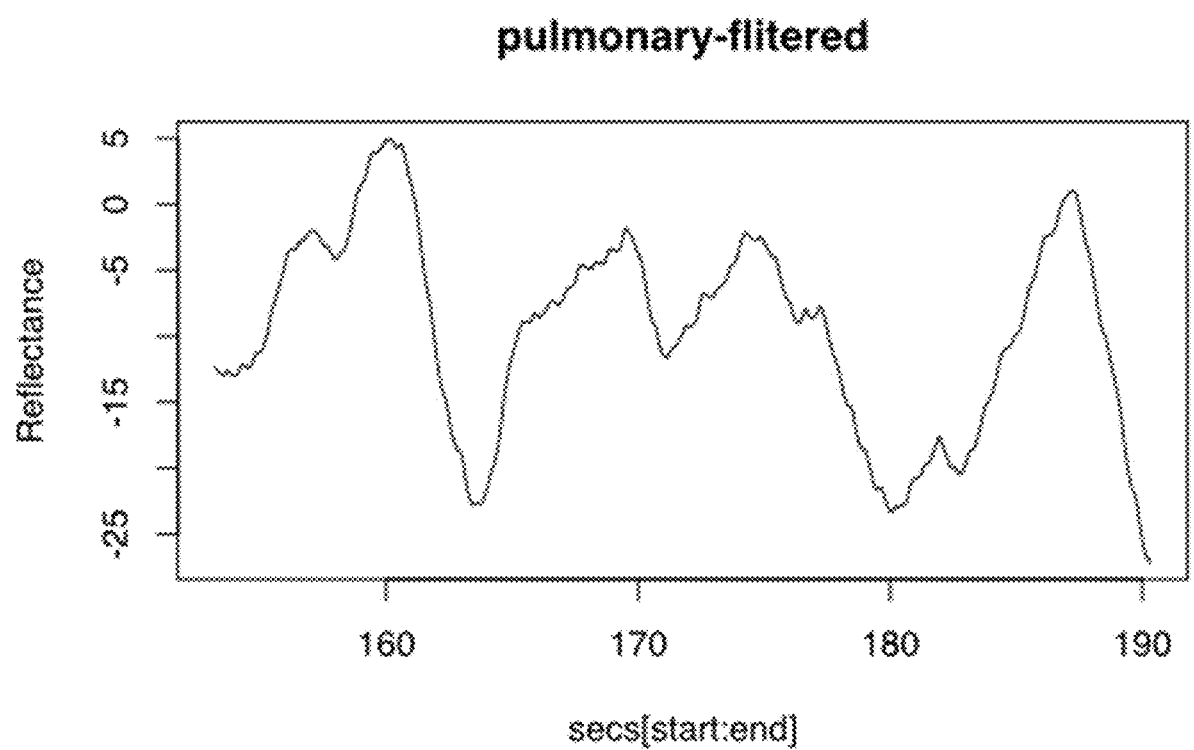

Folders of Raw pixel images (640×480 pixels) were batch processed with custom analysis scripts using the R framework. Grayscale values for each pixel across the individual frames were assembled into an array of (640×480=307200) individual pixel vectors. A series of filters were applied to enhance signal to noise ratio in the <1 Hz (for pulmonary activity) and 1-6 Hz (for cardiac activity) bands. A Butterworth band-pass filter was applied to reduce signal outside the frequency bands of interest. The filtered image was visualized. A power spectrum derived from Fast Fourier Transform (FFT) was used to identify the presence and strength of a recurring pattern, such as a heartbeat or breathing. Areas of the image in which neighboring pixels display strong rhythmic patterns in a 1-6 Hz range were identified. (FIGS. 2A-2D). Activity in the cardiac activity band of 1-6 Hz was visualized to identify the heartbeat. (FIG. 2C). Activity in the pulmonary activity band of <1 Hz was visualized to identify breathing. (FIG. 2D.) Recorded at 60 fps, the graphs in FIGS. 3A-3C illustrate repeating patterns of changes in IR reflectance in the cardiac activity band (FIG. 3B) and the pulmonary activity band (FIC. 3C). FIG. 3A depicts a raw trace, while FIGS. 3B-3C show the signal after signal processing and filtering. These signals were absent from other areas of the fly, and in the background away from the fly, indicating that the signal was not an artifact of the camera or lighting.

Figure 4A:
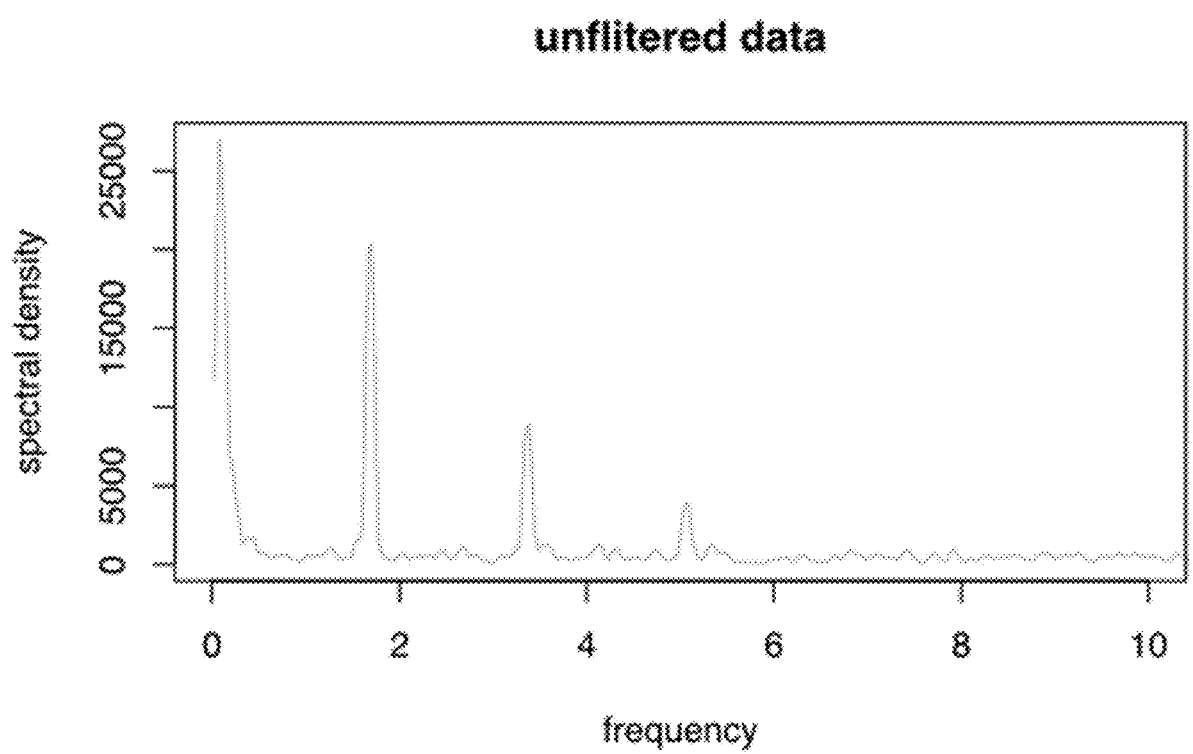
FIGS. 4A-4C: Graphs showing fourier spectrums from the signals before and after filtering.
Figure 4B:
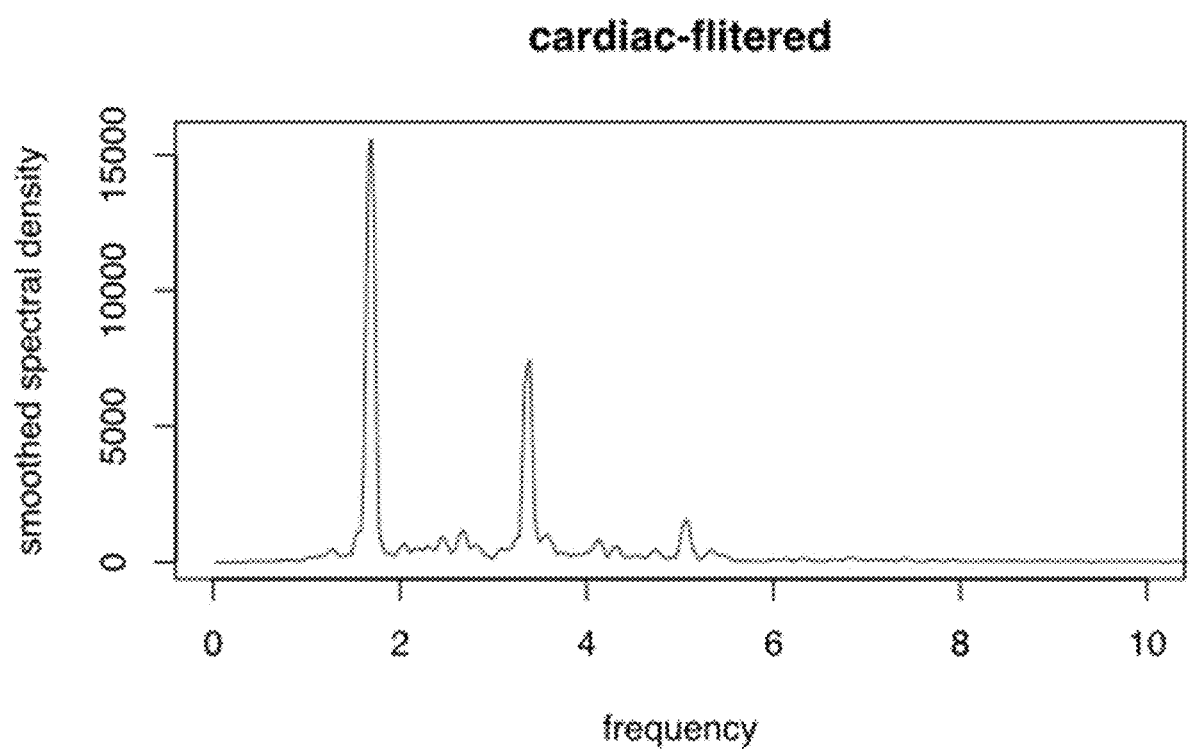
Figure 4C:
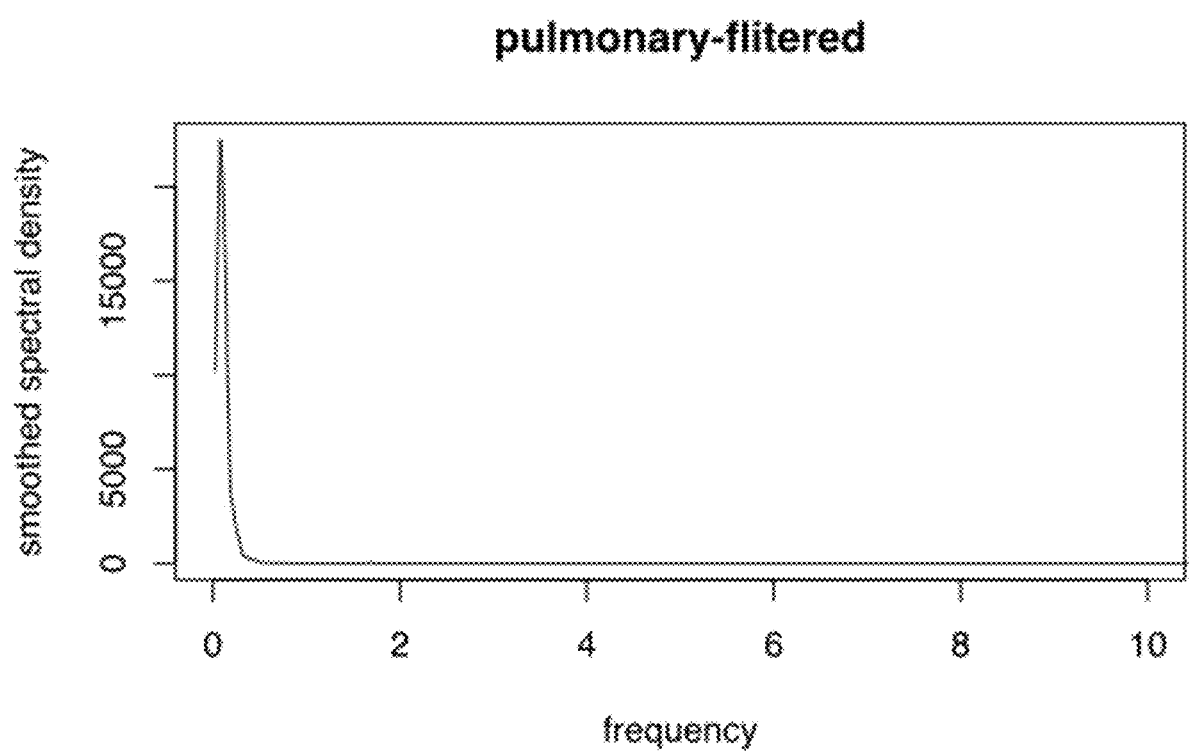

Sums of unfiltered and filtered pixel values for the neck region (15×15 pixels) were graphed over time to create fourier spectra. (FIGS. 4A-4C). FIG. 4B shows the cardiac-filtered fourier spectrum, and FIG. 4C shows the pulmonary-filtered fourier spectrum.

Certain embodiments of the systems and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the systems and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A method for analyzing cardiac activity or pulmonary activity of a fly, the method comprising:
    obtaining video of a neck region of a fly under infrared illumination to produce a stream of images; and
    identifying a recurrent pattern in the stream of images of the neck region of the fly, wherein the recurrent pattern corresponds to a heartbeat or breathing of the fly based on contractions and expansions of blood vessels within the neck region.

2. The method of claim 1, wherein the recurrent pattern has a frequency of <1 Hz and corresponds to breathing of the fly.

3. The method of claim 1, wherein the recurrent pattern has a frequency of 1-6 Hz and corresponds to the heartbeat of the fly.

4. The method of claim 1, wherein the video is obtained at a frame rate of at least 40 frames per second.

5. The method of claim 1, wherein the stream of images is assembled into an array of individual pixel vectors.

6. The method of claim 5, wherein the individual pixel vectors are filtered to enhance a signal-to-noise ratio and produce filtered images, and the recurring pattern is identified in the filtered images.

7. The method of claim 1, wherein the strength of the recurring pattern is identified with a fourier transformation.

8. The method of claim 1, wherein the infrared illumination is provided by an LED having a wavelength of 850 nm or longer.

9. The method of claim 1, wherein the video is obtained with a video camera that produces uncompressed images.

10. The method of claim 1, wherein the fly is immobilized.

11. A method of testing a pharmaceutical compound on an animal, the method comprising:
    administering a pharmaceutical compound to an animal, wherein the animal is a fly, a mouse, a fish, or an earthworm;
    observing the animal with video under infrared illumination to produce a stream of images of a neck region of the animal; and
    identifying a recurrent pattern in the stream of images, wherein the recurrent pattern corresponds to a heartbeat or breathing of the animal based on contractions and expansions of blood vessels within the neck region, to determine an effect of the pharmaceutical compound on the animal.

12. The method of claim 11, wherein the animal is a mouse, a fish, or an earthworm.

13. The method of claim 11, wherein the video is obtained at a frame rate of at least 40 frames per second.

14. The method of claim 11, wherein the animal is immobilized.

15. A method of evaluating a stimulus on a fly, the method comprising:
    observing a fly with video under infrared illumination to produce a stream of images of a neck region of the fly;
    applying a stimulus to the fly while observing the fly with video; and
    identifying a recurrent pattern in the stream of images, wherein the recurrent pattern corresponds to a heartbeat or breathing of the fly based on contractions and expansions of blood vessels within the neck region, to determine an effect of the stimulus on the heartbeat or breathing of the fly.

16. The method of claim 15, wherein the stimulus comprises exposure to light, heat, cold, an odor, physical touching, or a sound.

17. The method of claim 15, wherein the stimulus comprises an electric shock, food or water deprivation, social stress, or stressful environmental conditions.

18. The method of claim 15, wherein the fly is immobilized.

19. A method for analyzing pulmonary activity of a fly, the method comprising:
    obtaining video of a neck region of the fly under infrared illumination to produce a stream of images; and
    identifying a recurrent pattern in the stream of images of the neck region of the fly, wherein the recurrent pattern corresponds to breathing of the fly based on contractions and expansions of blood vessels within the neck region.

* * * * *